(12) United States Patent
Bacus et al.

(10) Patent No.: US 8,306,300 B2
(45) Date of Patent: *Nov. 6, 2012

(54) FOCUSABLE VIRTUAL MICROSCOPY APPARATUS AND METHOD

(75) Inventors: James V. Bacus, Downers Grove, IL (US); James W. Bacus, Oakbrook, IL (US)

(73) Assignee: Olympus America Inc., Center Valley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/083,062

(22) Filed: Apr. 8, 2011

(65) Prior Publication Data

US 2011/0181622 A1  Jul. 28, 2011

Related U.S. Application Data

(63) Continuation of application No. 12/549,797, filed on Aug. 28, 2009, now Pat. No. 7,925,067, which is a continuation of application No. 10/373,156, filed on Feb. 24, 2003, now Pat. No. 7,596,249.

(60) Provisional application No. 60/358,747, filed on Feb. 22, 2002.

(51) Int. Cl.
*G06K 9/00* (2006.01)
(52) U.S. Cl. ......... 382/128; 382/133; 382/284; 382/294
(58) Field of Classification Search .................. 382/128, 382/133, 284, 294
See application file for complete search history.

(56) References Cited

U.S. PATENT DOCUMENTS 3,999,047 A   12/1976   Green
4,150,360 A    4/1979   Kopp
(Continued)

FOREIGN PATENT DOCUMENTS
EP         0209422          1/1987
(Continued)

OTHER PUBLICATIONS

Szeliski, "Image Mosaicing for Tele-Reality Applications", Proceedings of the IEEE Workshop on Applications of Computer Vision, XX, XX, May 1, 1994, pp. 44-53.

(Continued)

*Primary Examiner* — John Strege
(74) *Attorney, Agent, or Firm* — Meagher Emanuel Laks Goldberg & Bovino, LLP

(57) ABSTRACT

A virtual microscope slide includes images of a specimen for a given level of optical magnification which are associated and stored in a data structure. The forming of the data structure having the multiple Z-plane images preferably includes automatically focusing at a principal reference focal plane and capturing and digitizing an optically magnified reference Z-image and then shifting the specimen relative to the lens system by a predetermined increment to capture and digitize another Z-plane image. Preferably, a multiple sequence of Z-plane images above and below the reference image and captured and digitized. For ease of retrieval and use, each reference image has its associated Z-plane images are formed in a stack that is sent over the Internet, or Intranet to a local computer storage for quick retrieval when a viewer wants to mimic a focusing up or down to better view a detail in an image. Thus, the resultant images are retrieved and displayed such that a virtual focusing capability is available to the user. The images can be formed with overlapping fields of depth, adjacent fields of depth, or wholly separated fields of depth.

22 Claims, 7 Drawing Sheets

U.S. PATENT DOCUMENTS

Figure 1:
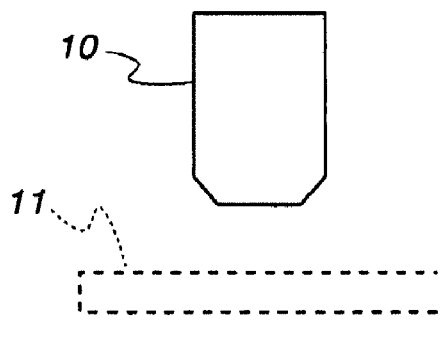

| | | | |
|---|---|---|---|
| 4,175,860 A | 11/1979 | Bacus |
| 4,199,748 A | 4/1980 | Bacus |
| 4,213,036 A | 7/1980 | Kopp |
| 4,523,278 A | 6/1985 | Reinhardt |
| 4,742,558 A | 5/1988 | Ishibashi |
| 4,760,385 A | 7/1988 | Jansson |
| 4,777,525 A | 10/1988 | Preston, Jr. |
| 4,887,892 A | 12/1989 | Bacus |
| 4,965,725 A | 10/1990 | Rutenberg |
| 5,016,109 A | 5/1991 | Gaylord |
| 5,018,209 A | 5/1991 | Bacus |
| 5,068,906 A | 11/1991 | Kosaka |
| 5,072,382 A | 12/1991 | Kamentsky |
| 5,073,857 A | 12/1991 | Peters |
| 5,099,521 A | 3/1992 | Kosaka |
| 5,107,422 A | 4/1992 | Kamentsky |
| 5,123,056 A | 6/1992 | Wilson |
| 5,163,095 A | 11/1992 | Kosaka |
| 5,216,500 A | 6/1993 | Krummey |
| 5,216,596 A | 6/1993 | Weinstein |
| 5,218,645 A | 6/1993 | Bacus |
| 5,252,487 A | 10/1993 | Bacus |
| 5,257,182 A | 10/1993 | Luck |
| 5,260,871 A | 11/1993 | Goldberg |
| 5,268,966 A | 12/1993 | Kasdan |
| 5,287,272 A | 2/1994 | Rutenberg |
| 5,297,034 A | 3/1994 | Weinstein |
| 5,313,532 A | 5/1994 | Harvey |
| 5,333,207 A | 7/1994 | Rutenberg |
| 5,428,690 A | 6/1995 | Bacus |
| 5,473,706 A | 12/1995 | Bacus |
| 5,499,097 A | 3/1996 | Ortyn |
| 5,505,946 A | 4/1996 | Kennedy |
| 5,544,650 A | 8/1996 | Boon |
| 5,625,765 A | 4/1997 | Ellenby |
| 5,655,029 A | 8/1997 | Rutenberg |
| 5,687,251 A | 11/1997 | Erler |
| 5,784,162 A | 7/1998 | Cabib |
| 5,793,969 A | 8/1998 | Kamentsky |
| 5,796,861 A | 8/1998 | Vogt |
| 5,836,877 A | 11/1998 | Zavisian |
| 5,838,837 A | 11/1998 | Hirosawa |
| 5,883,982 A | 3/1999 | Riley |
| 5,978,804 A | 11/1999 | Dietzman |
| 5,993,001 A | 11/1999 | Bursell |
| 6,078,681 A | 6/2000 | Silver |
| 6,091,842 A | 7/2000 | Domanik |
| 6,091,930 A | 7/2000 | Mortimer |
| 6,101,265 A | 8/2000 | Bacus |
| 6,148,096 A | 11/2000 | Pressman |
| 6,151,405 A | 11/2000 | Douglass |
| 6,272,235 B1 | 8/2001 | Bacus et al. |
| 6,711,283 B1 | 3/2004 | Soenksen |
| 6,864,065 B2 | 3/2005 | Kim |
| 6,917,696 B2 | 7/2005 | Soenksen |
| 7,027,628 B1 | 4/2006 | Gagnon |
| 7,035,478 B2 | 4/2006 | Crandall |
| 7,596,249 B2 * | 9/2009 | Bacus et al. | 382/128 |
| 7,925,067 B2 * | 4/2011 | Bacus et al. | 382/128 |

FOREIGN PATENT DOCUMENTS

| | | |
|---|---|---|
| EP | 0246010 A | 11/1987 |
| JP | 02004285 | 1/1990 |
| JP | 05303621 | 11/1993 |
| JP | 05313071 | 11/1993 |
| JP | 05-333271 | 12/1993 |
| JP | 06003601 | 1/1994 |
| JP | 06051209 | 2/1994 |
| JP | 06118307 | 4/1994 |
| JP | 07015721 | 1/1995 |
| JP | 07333522 | 12/1995 |
| JP | 09-196621 | 7/1997 |
| JP | 2000-039566 | 2/2000 |
| JP | 2000-162504 | 6/2000 |
| JP | 2000-316120 | 11/2000 |
| JP | 2000-357229 | 12/2000 |
| JP | 2001-298755 | 10/2001 |
| WO | 9839728 | 8/1998 |
| WO | 9930264 | 6/1999 |
| WO | 0105452 | 7/2001 |

OTHER PUBLICATIONS

Krishnan et al., "Panoramic Image Acquisition" Proceedings 1996 IEEE Computer Society Conference on Computer Vision and Pattern Recognition (CAT No. 96CB35909), Proceedings of IEEE Conference on Computer Vision and Pattern Recognition, San Francisco, CA, USA, Jun. 18-20, 1996.

Szeliski et al., "Direct Methods for Visual Scene Recognition" Digital Equipment Corporation Cambridge Research Lab, Jun. 24, 1995, pp. 26-33.

Dani et al., "Automated Assembling of Images: Image Montage Preparation" Department of Electrical Engineering, Indian Institute of Technology, Oct. 24, 1993, pp. 431-445.

Boone et al., "Biomarkers of Premalignant Breast Disease and Their Use as Surrogate Endpoints in Clinical Trials of Chemopreventive Agents" The Breast Journal, vol. 1, No. 4, (1995), pp. 228-235.

Pressman, "Markovian Analysis of Cervical Cell Images", The Journal of Histochemistry and Cytochemistry, vol. 24, No. 1, (1976), pp. 138-144.

Bacus, "The CAS 200th Multiscan Automated Pathology Workstation" Compendium on the Computerized Cytology and Histology Laboratory, Tutorials of Cytology, copyright 1994.

Laferty, "Digital Composite Imaging for High Resolution Specimen Analysis", The Journal of NIH Research, vol. 6, No. 11, Nov. 3, 1994, p. 78.

Henderson et al., "Image Acquisition of Microscopic Slides, Proceedings of the SPIE", The International Society for Optical Engineering, vol. 2173, (1994), pp. 21-27.

Young et al, "Implementing a Collaboratory for Microscopic Digitial Anatomy", The International Journal of Supercomputer Applications and High Performance Computing, vol. 10, No. 2/3, Sage Publications, Inc., 1996, pp. 170-181.

Fan et al, "Telemicroscopy, Ultramicroscopy", Elsevier Science Publishers B.V., vol. 52, 1993, pp. 499-503.

* cited by examiner

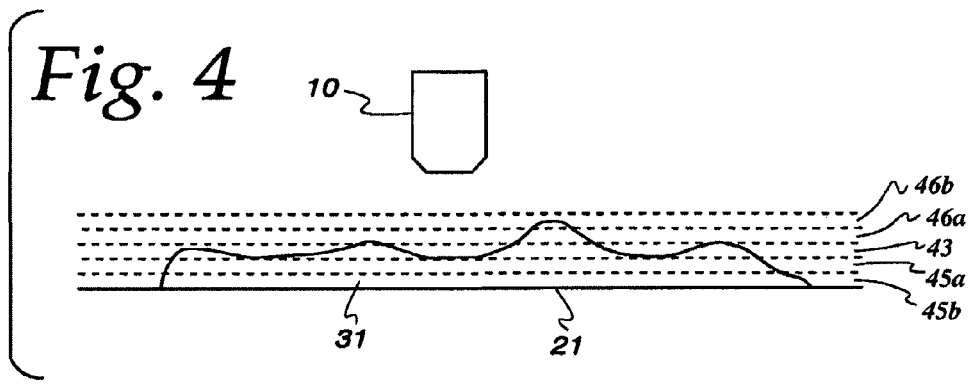
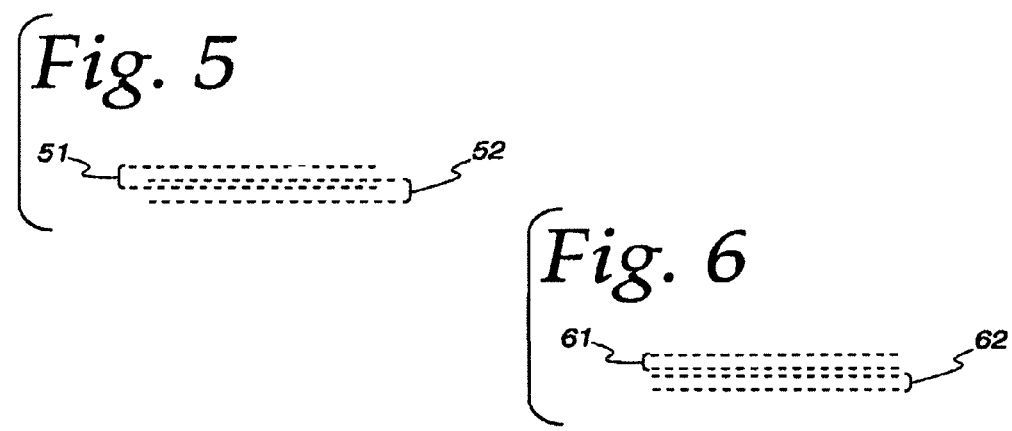
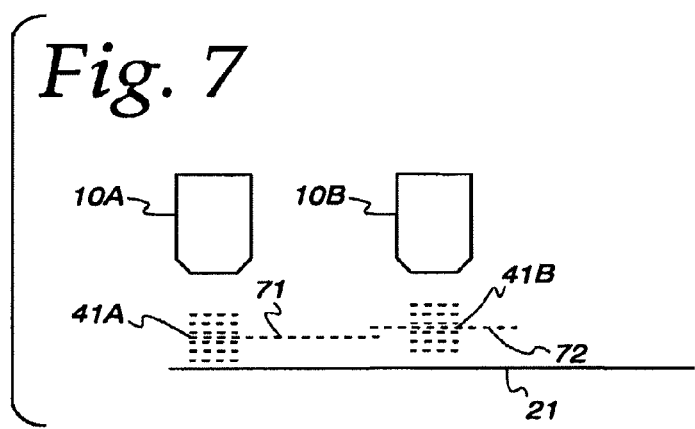

FOCUSABLE VIRTUAL MICROSCOPY APPARATUS AND METHOD

CROSS REFERENCE TO RELATED APPLICATIONS

This application is a continuation of U.S. patent application Ser. No. 12/549,797, filed Aug. 28, 2009, now U.S. Pat. No. 7,925,067, issued Apr. 12, 2011, which is a continuation of U.S. patent application Ser. No. 10/373,156, filed Feb. 24, 2003, now U.S. Pat. No. 7,596,249, issued Sep. 29, 2009, which claims the benefit of U.S. Provisional Application No. 60/358,747, filed Feb. 22, 2002, which are incorporated by reference as if fully set forth.

FIELD OF INVENTION

This invention relates to a method of, and an apparatus for, acquiring and constructing virtual microscope slides that include a Z-axis image dimension across the entire virtual slide, from a specimen on a support, such as a glass microscope slide, such Z-axis image content being relative to multiple individual principal, or reference, image focal positions across the glass microscope slide; and for storing, and transferring the virtual microscope slide images including a coordinated and seamless in the X, Y-plane of a Z-axis dimension, for viewing by another to allow virtual focusing at a local or remote location.

BACKGROUND

Magnification of small objects using a microscope is well known. Microscopes facilitate magnification of small objects to thereby allow details of the small objects to be rendered visible. At any given magnification, a microscope has a corresponding field of view. In general, the greater the amount of magnification the smaller the corresponding field of view relative to the object. Similarly, and as represented in FIG. 1, at any given focal distance, a microscope objective lens (10) has a corresponding focal plane with a depth of field (11) (that is, a Z-axis range within which objects will appear to be in focus). In general also, the greater amount of magnification the smaller the corresponding depth of field relative to the object. The capture of single digital images of these microscope fields of view is well known, and the art is experienced with the capture and display of stacks of images at a single object position to record depth of field image content. Such images are used for example in confocal microscopy instruments to image through objects by varying the Z-axis focal position of each image in the image stack at a single X, Y planar location.

In the early microscope technology, around 1750, microscope specimens were placed between 2 small, thin circular glass plates, and mounted on long ivory "sliders" that could be pulled back and forth in a slot under the microscope objective lens. With today's technology the sliders have been replaced by rectangular glass "slides" as a mounting structure, the object specimen is placed on the slide and sometimes covered by a thinner glass "coverslip". These glass slide mounting structures are not flat over their entire surface area, i.e., within the tolerances of the depth of field of a common 40× to 100× microscope objective lens. They are thicker in some portions than in others and sometimes have a warp or curvature. This creates a significant problem in the construction of a virtual microscope slide in contrast to taking a single field of view image. This is because in most instances the Z-axis focal plane of the objective will not be positioned in the same cross sectioned portion of the specimen, and thus not be "in focus" across the entire surface of the slide, i.e., in adjacent planar X, Y field of views, without adjusting the specimen in the Z-axis dimension in some manner. For example, in the simple case of one end of the slide being thicker than the other end, all other factors being equal, and assuming the stage support is flat, this produces a slope across the slide with regard to positioning the same portion of the cross section of the specimen in the objectives focal plane. This is not a problem for single field of view multiple Z dimension images because the slope is not apparent in the small field of view. Another aspect of this problem relates to the stage support. Stages commercially available are often not parallel and flat across the complete working distance of the commonly used glass microscope slides. Also microtome sectioning does not produce uniformly thick sections. So in cross section the thickness of the specimen object varies. Thus the proper focal plane can vary from place to place on the slide from a multitude of factors. The focal distance position is determined by the microscope objective lens, and although the lens could move to adjust the focal plane position, it is common to move the stage platform that holds the glass slide structure up and down in the Z direction to obtain the optimal focal plane for a given specimen location and single field of view, or image tile. Thus, as is well known in the art, the focal plane position in the Z-axis, relative to the microscope slide planar surface and deposited specimen thereon varies substantially from point to point for accurate focus in a give specimen.

Virtual microscope slides are also known. U.S. Pat. No. 6,272,235 B1 (entitled Method and Apparatus for Creating a Virtual Microscope Slide), the contents of which are incorporated herein by this reference, teaches the creation, storage and Internet or intranet display of virtual microscope slides. As taught therein, a virtual microscope slide typically comprises a digitized magnified view of part or all of a microscope slide and an object (such as a biological specimen) disposed thereon. Virtual microscope slides; when created, overcome limitations of the microscope optical field of view restrictions; they have a data structure for storing the digital images from different parts of the slide to enable the reconstruction of an X, Y planar view from composite image parts; and when viewed, overcome the limitations of the finite size of computer terminal display screens, with Internet or intranet viewer software that seamlessly and rapidly allows the user to navigate from place to place in the virtual image, and to zoom the virtual image to mimic changing of magnification with different microscope objectives. Prior art virtual slides allow computer viewing to mimic the viewing and inspection process obtained by looking through a real microscope with respect to viewing abutted, aligned X, Y planar image views.

As taught in the aforesaid patent, the area of the object digitized is comprised of multiple, adjacent, microscope objective optical fields of view captured at a single Z-plane focal distance. In some cases thousands of microscope objective optical fields of view are recorded to represent the virtual microscope slide. As taught in the aforesaid patent, the individual digitized fields of view are referred to as tiles. The chosen Z-plane object position varies for a given tile with the X, Y location on the microscope slide, and as taught in the aforesaid patent, is obtained as a representative, reasonably optimum, focal position choice by an automatic focusing determination on individual image fields, or by extension from previously determined focal positions of nearby image fields. The object is digitized and the resulting images stored in a data structure that allows for subsequent retrieval for review or image processing.

Because of the limitations of the microscope objective lens optics field of view, the capture event of virtual microscope slide tiles is always restricted to only a small part of the object in at least one planar dimension. As further taught in the aforesaid patent, the digital capture was with a 3 color chip CCD sensor, which enabled the same object area sampled pixel point in and individual tile to be captured as 3 identical color pixels, in register with each other. In an alternative embodiment of a scanning method not taught in the aforesaid patent, a line sensor, e.g., with dimensions of 3×2098 pixels, could be used and moved in one direction at a constant speed, and the sampling could be performed to acquire a series of tiles of dimension 3×2098 stored in computer memory to form a larger image segment. However, this image segment is still limited in one direction by the optical field of view, and subsequent adjacent tiled image segments are acquired to construct the virtual microscope slide. In this case the 3 pixels at each given position along the line sensor provide different color sensing, thus there is a small loss of color and spatial information with this method. As is known in the art, other combinations of sensor sampling can be obtained. However to construct a truly virtual microscope slide image capture that can be reconstructed to abut captured image portions, the method must overcome the limitation of the very small optical field of view in at least one dimension of the object plane of the microscope objective lens at high magnifications. Typically this is accomplished by either moving the stage or the microscope objective to cover the object area and construct the digitized image data structure.

It may be further appreciated that the digitized image data structure may be stored in numerous ways to facilitate future viewing. One method may be to simply store each capture event in a very large contiguous digital memory or storage. In this case the subsequent viewing may be accomplished by simply indexing this memory and displaying standard 2 dimensional images, e.g., of X by Y pixel size, on a computer screen. However, with this method the virtual slide Internet server memory requirements become very large. As described in the aforesaid patent a tiled data structure is more efficient of server memory and Internet transmission speed.

It is additionally taught in the aforesaid patent, that the standard computer video display will also only display a small portion of the total virtual slide at the original capture resolution, or highest magnification. To overcome this, various methods of image data structure and storage have been described, and typically the viewer program can zoom in and out to display high and low magnification fields, and can cache portions of the virtual slide image data that have been previously transmitted from digital storage or an Internet server and viewed. The viewer display programs must handle the indexing and addressing to bring in only the user requested image portions. Also, the virtual microscope slide can be scrolled in various directions and thereby mimic movement of the object/slide with respect to the microscope objective lens. Such virtual microscope slides can be used for a variety of purposes, including education, training, and quantitative and qualitative analysis.

For many applications, such virtual microscope slides work well, and especially with specimens that are of relatively uniform thickness and with features of interest that tend to be within a single depth of field. Such virtual microscope slides solve the first of two significant technological issues of virtual microscopy; the first being the issue of aligning small adjacent image segment views and displaying them seamlessly in X, Y registration. For any given level of magnification, the microscope can be automatically focused on such a specimen and the corresponding single focal plane image digitally captured and stored for later retrieval and use.

When the specimen exhibits significantly varying depth, however, and/or where features of interest are more widely spaced with respect to depth, prior art virtual microscope slides may contain images that are not fully focused with respect to one or more desired elements. This is the second major technical issue with virtual microscopy; the issue being finding the proper focal plane to represent the image in the first place, or alternatively including the Z-axis dimension across the entire slide and in so doing in either case, overcoming the problem of a non-flat microscope glass slide support and the problem of tissue sectioning and deposition irregularities that change the position of the optimum focal plane relative to the planar X, Y surface of the glass slide. Consistent with the inherent problems of this second issue, obtaining stacks of Z-plane images in an uncoordinated fashion from many different non-abutting object positions, without an integrated virtual slide data structure is both difficult to adequately store and retrieve, and to view in a coherent fashion in an Internet or internet environment. For example, and with reference to FIG. 2, a microscope slide (21) can bear a specimen having portions (22) of relatively even depth, or Z-axis position, and/or portions (23) that vary significantly with respect to depth. While some portions (22) may reside within the depth of field (11), other portions (26 and 27) that extend above or below the depth of field (11) will likely appear unfocused in the resultant image. Similarly, features of interest (24) that occur within the depth of field (11) will appear focused but features of interest (25) that are outside the depth of field range may appear unfocused. Regardless of whether such a virtual microscope slide is being used academically, for tissue microarray imaging, as in U.S. Pat. No. 6,466,690 B2, or with diagnostic intent, unfocused elements often render such an image unsuitable for the desired activity.

SUMMARY

In accordance with the present invention, there is provided a new and improved method and apparatus for constructing, storing, and then viewing virtual microscope slides from a microscope specimen that includes the capture of multiple Z-plane images to preserve depth of field image content. The improved method and apparatus also includes storing the data structure of the individual tiled, or captured images in a format that includes the Z-plane images but is relative to a chosen optimal image tile, allowing for full reconstruction of adjacent areas in multiple Z-planes, and enabling an Internet virtual microscope server to efficiently transfer the virtual slide images with multiple Z-planes for viewing by another at a remote location. This is achieved in the preferred embodiment as a multiple Z-axis sequence of image captures, referenced by an automatically obtained chosen Z-axis focus position of a single tile at a given X, Y position, as such scanning is taught in the aforementioned patent. Multiple Z-plane images are captured above and below the given reference tile, and associated with it in the data structure.

The preferred data structure is also provided with a proprietary virtual slide Internet/intranet Browser and generic component panel viewing programs, e.g., an ActiveX component and Java Applet, all of which allow the remote user to manipulate the Z-axis image dimension when viewing virtual slide images, either in the proprietary Internet/intranet Browser, or in the users own application programs or general purpose Internet/intranet Browsers. The data structure may be transmitted over the Internet or intranet so that users may focus up or down at a given object position to view the virtual slide specimen throughout a Z-axis depth, and thus bring objects and detail into focus that cannot be seen with just one recorded Z depth of focus tile. In the preferred embodiment of this invention such viewing can be accomplished by moving a computer mouse wheel back and forth, or by moving through different Z-axis images with computer keyboard up or down arrows. Further the viewing programs allow the user to scroll and to view neighboring image areas of neighboring tiles and view the associated Z-axis images.

Turning now in greater detail to aspects of the invention, problems with achieving the additional Z-axis image content relative to the principal image focal plane are overcome by the system of the invention. The system includes a microscope stage which holds and supports the glass slide (21) at a certain fixed distance below the microscope objective (10), so that the specimen on the glass slide has an appropriate object within the depth of focus (11) for the given microscope objective. The microscope stage is computer controlled by precision stepping motors in the X, Y plane and also in the Z-axis dimension. Scanning in the X, Y plane with the preferred method of this invention occurs by moving the stage with the X, Y stepping motors precisely from one image field of view to another to acquire image tiles. The step sizes for each x or y movement occur in predetermined incremental step sizes so that the tiles abut and align with one another. Since the glass slide is held and supported firmly by the stage, and the specimen is held firmly on the glass slide, the effect is to move the glass slide and thus new specimen parts into the field of view of the microscope objective. However, the content of the image is subject to the given depth of focus (11) of the objective. Specimen parts in the field of view, but outside of the depth of focus region are not included in the image content. The microscope stage which supports the microscope slide is also controlled in the Z-axis direction so that it can move the specimen parts in a field of view on the slide that are not in the Z-axis depth of focus region, into the Z-axis depth of focus region as desired. Movement of the microscope stage in the Z-axis is computer controlled in digital increments of Z-axis step size. Each digital unit represents the smallest incremental step possible. For example, in one automated microscope system, the Olympus BX61 (sold by Olympus America Inc. 2 Corporate Center Drive, Melville, N.Y. 11747, USA) with the internal motorized Z-drive, one increment represents 0.01 um. During the setup phase, prior to scan initiation certain Z-axis step size parameters are defined for automatic focus, and for a subsequent Z Stack image tile save procedure. For any given tile the Z Stack save procedure saves a set of 4 image tiles above a given reference Z-axis position and 4 image tiles below that Z-axis reference position. Each image tile in the set is separated from the next in the Z-axis dimension by the Z-axis step size parameter. The relative reference position for each new field of view tile is obtained by an iterative automatic focus procedure as follows. Upon moving to the next tile, the Z-axis focus position is incrementally changed to go up 4 times in automatic focus step sizes and acquire an image at each step and then to go down in automatic focus step sizes and acquire an image at each step. A focus contrast parameter is computed on each image. The automatic focus position is then determined by choosing the Z-axis position associated with the largest value of the focus parameter from the reference image and the set of 8 image tiles. If the largest value is at one end of the sequence, the procedure is recursively repeated until the largest value is found in the middle range of the sequence of tiles. This becomes the reference tile image. At that point the system proceeds to use the Z-axis step size and execute the Z Stack save procedure. These Z stack image planes are added to the tiled image data structure, and associated with the reference tile so that they can be easily accessed for later retrieval and display. The same series of events is repeated for all field of views associated with the capture of the virtual microscope slide.

The step sizes chosen as input parameters for the scan relate to the Z-axis incremental resolution of the microscope system, to the chosen microscope objective lens, and to the requirements of the specimen, determined primarily by the sectioning thickness of tissue sections or the smear thickness of blood or cell smears. For example, an incremental Z-axis size of 0.01 um, with an automatic focus step size of 40 units would provide a travel range of 1.6 um up and 1.6 um down, for a total travel in one sequence of 3.6 um in a tissue section. This can be compared for example to a commonly used tissue section thickness of 5 um. A Z stack step size of 20 would then similarly result in a focus range of 1.8 um that could be examined virtually in 9 discreet and different depth of field focal planes, according to the apparatus and—method of the invention.

It should be appreciated that the 2 step procedure of first determining a next relative focus position, and then recording the full chosen Z stack range allows for the compensation of irregularities caused by non-flatness of the glass slide substrate, and by uneven tissue sectioning and deposition of clumped cells in blood and in smear preparations. This preferred method including the recursive aspect, and different adjustable Z-axis step sizes for the automatic focus, and then for the Z Stack capture, also enable a robust tracking up and down reference focal depth of field slopes in the specimen. The preferred method also allows for an efficient storage of image information that effectively increases the usable image content in the Z-axis dimension. This is especially true for very thick specimens, such as plant material mounted on a glass slide, or thick sections including whole mounts of small organisms and insects. When used with the virtual slide Internet server and viewer software the preferred method allows for efficient user visual inspection and viewing of the additional Z-axis image content

BRIEF DESCRIPTION OF THE DRAWING(S)

Figure 2:
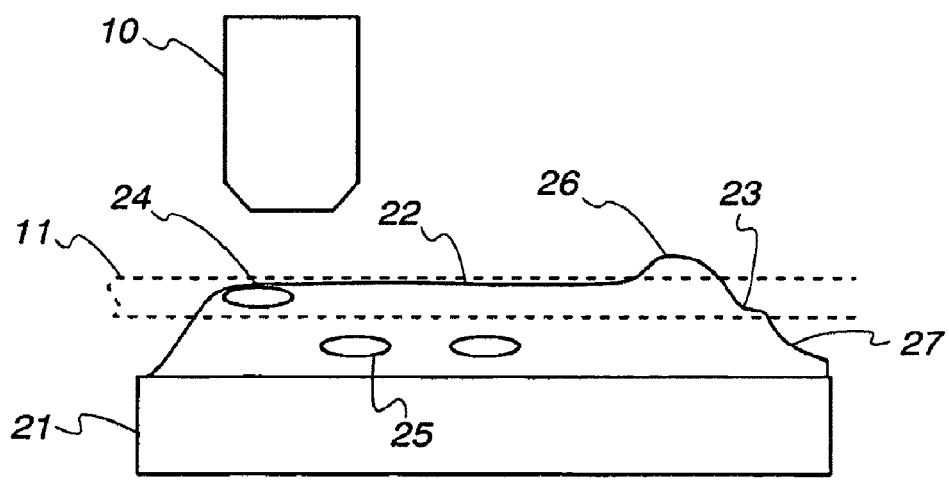
Figure 3:
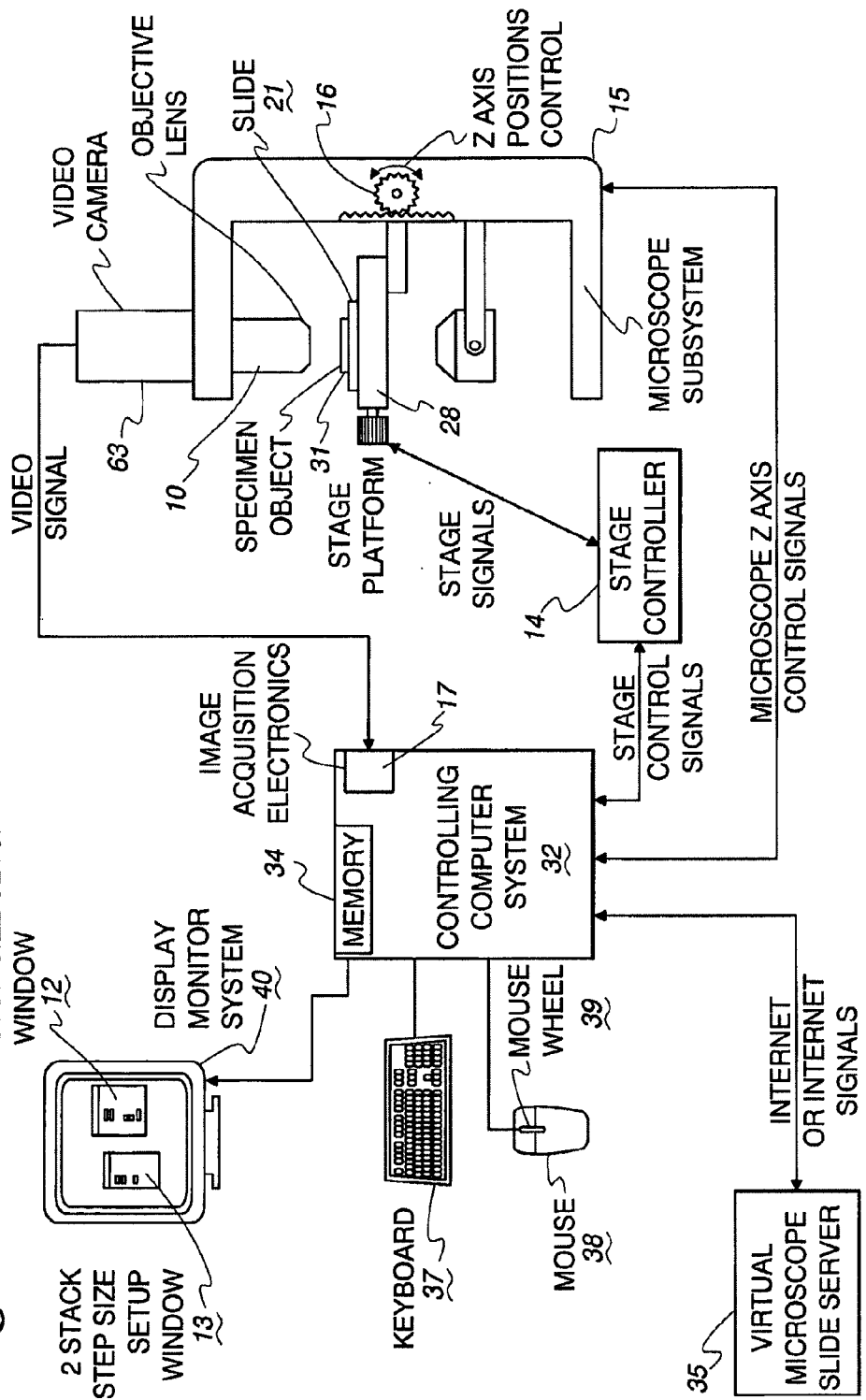
Figure 3A:
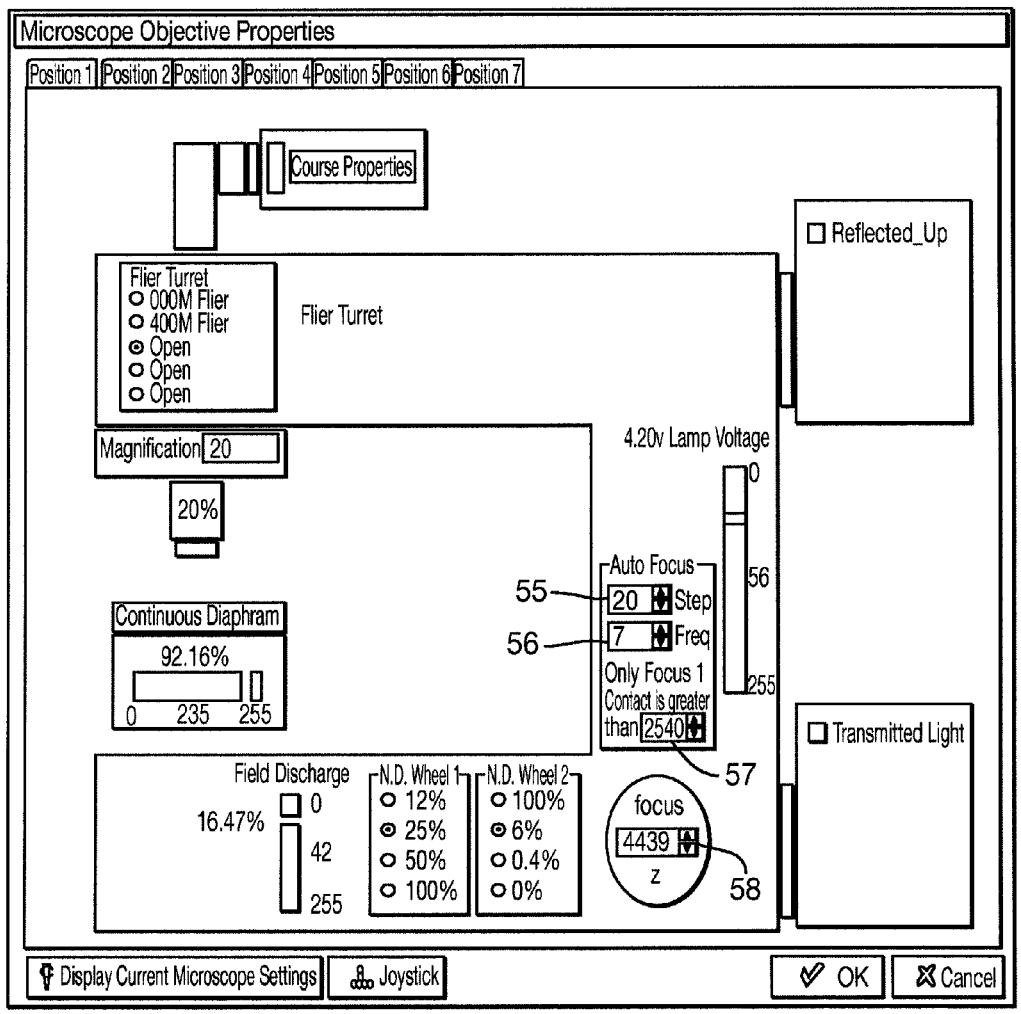

FIG. 1 comprises a depiction of a prior art microscope objective and a corresponding depth of field in the focal plane of the objective;

FIG. 2 comprises a prior art depiction of a specimen on a microscope slide showing object detail in the specimen inside of and outside of the depth of field;

FIG. 3 comprises a block diagram depiction of an embodiment configured in accordance with the invention;

FIG. 3A comprises a window that allows the automatic focus setup step size parameter to be input.

Figure 3C:
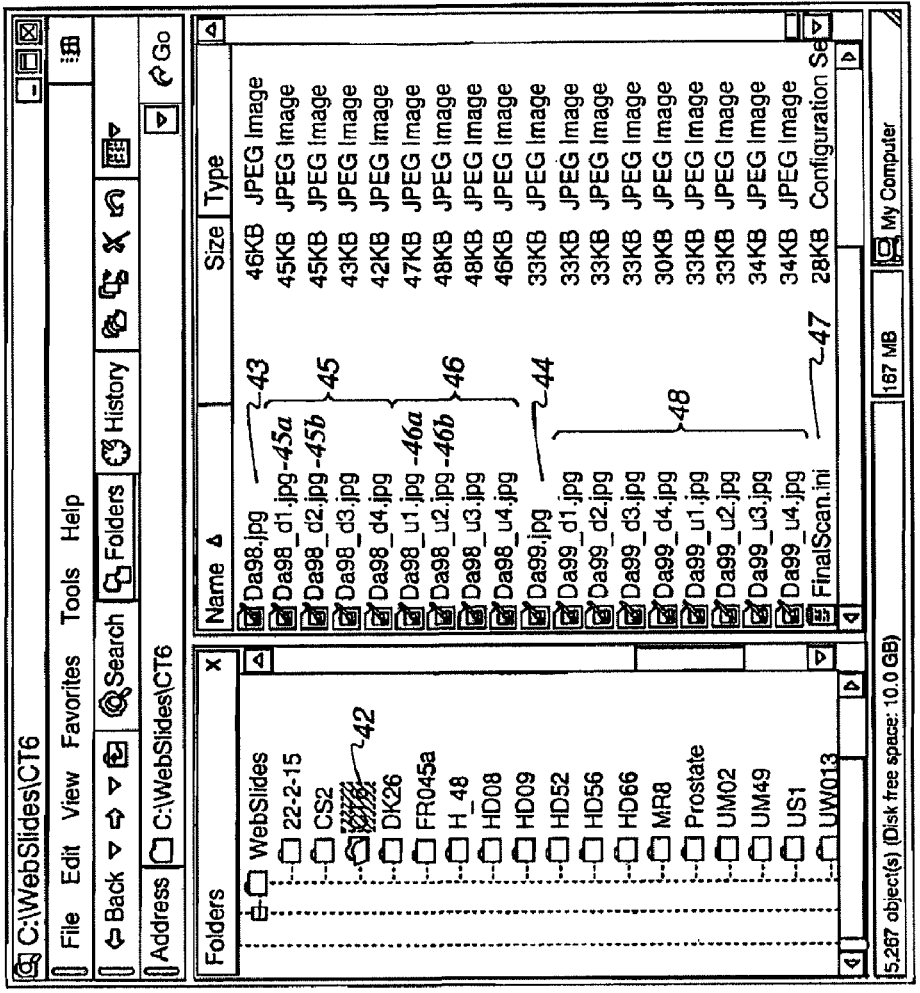
Figure 3B:
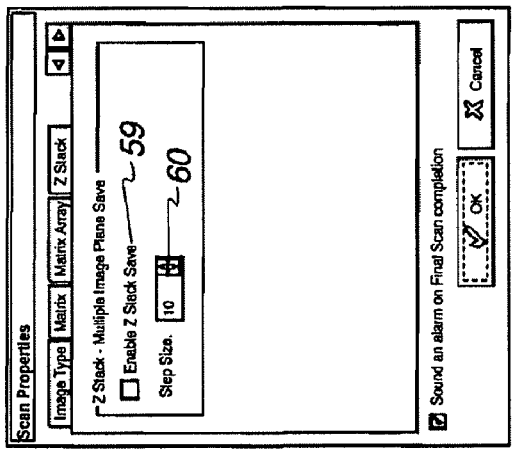

FIG. 3B comprises a window that allows the Z Stack setup step size parameter to be input.

FIG. 3C comprises an example of a virtual slide folder with part of the data structure showing the correspondence between the reference data structure image tile, the Z-axis dimension focus data structure image tiles, and the .ini data file for the given virtual slide.

Figure 8:
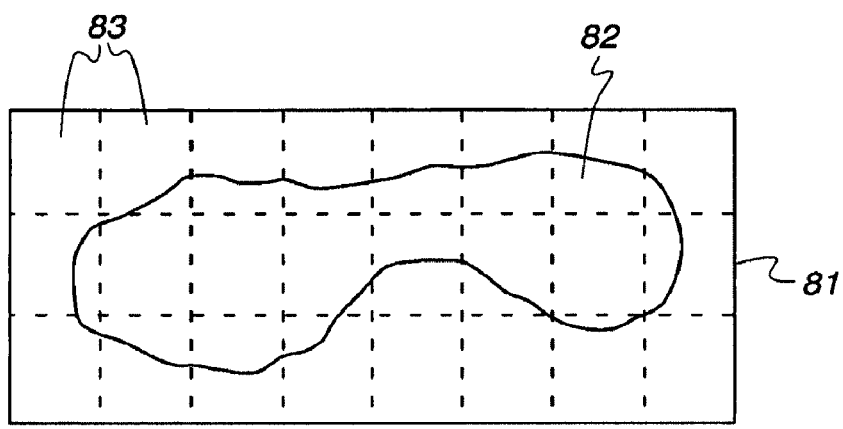
Figure 9:
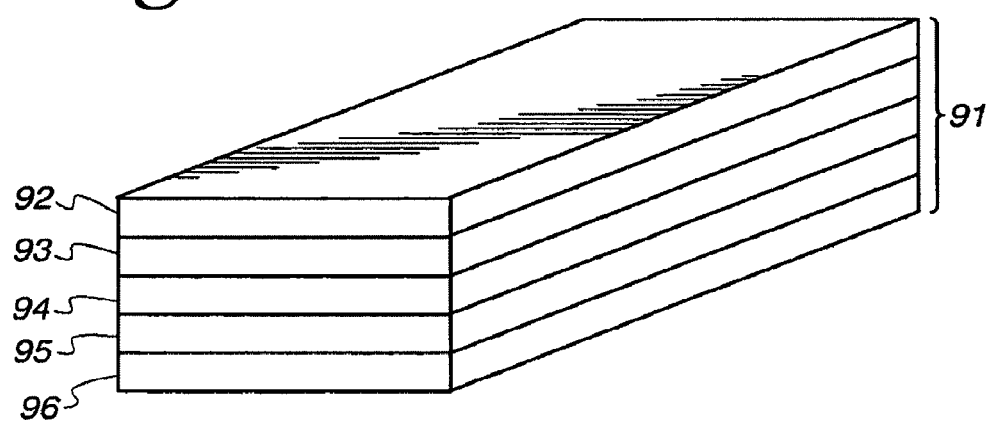
Figure 10:
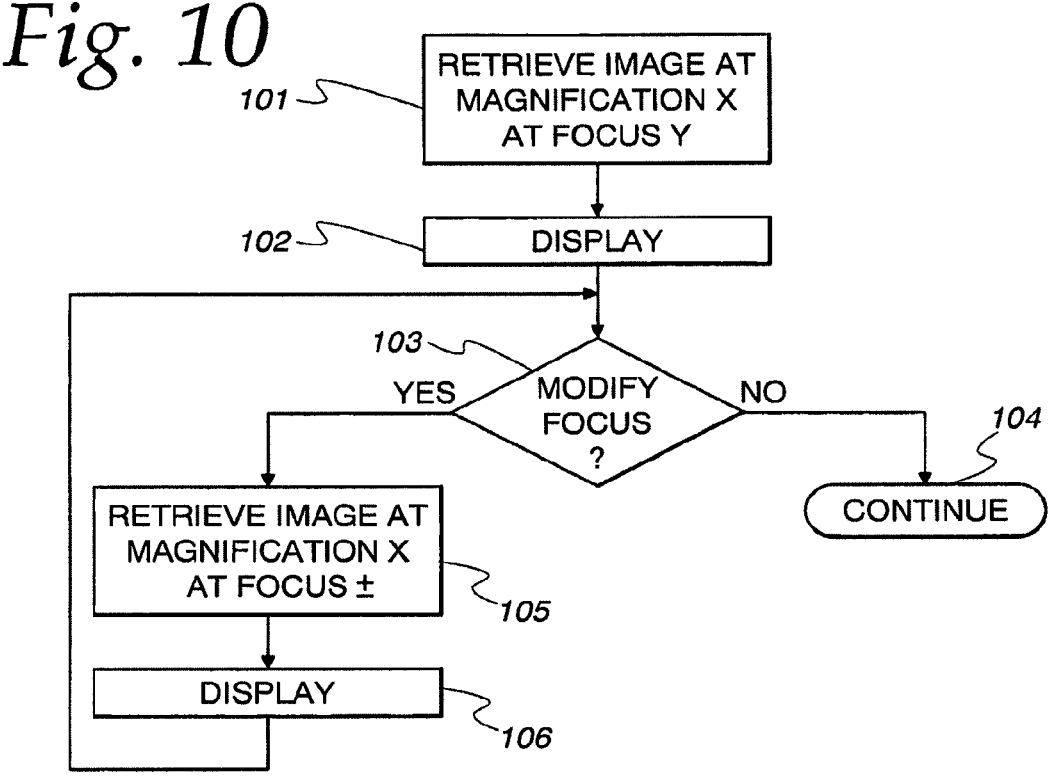
Figure 11:
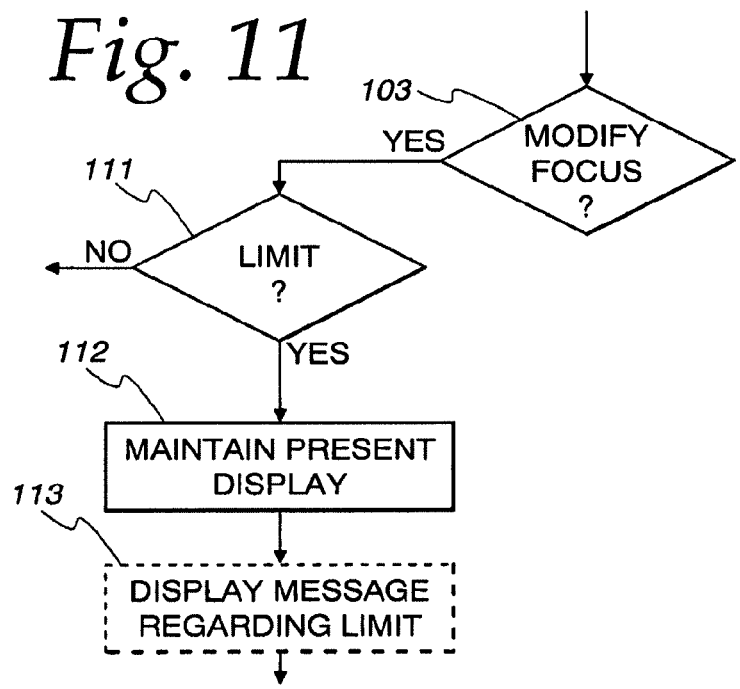

FIG. 4 comprises a side elevation view of a specimen on a microscope slide in an embodiment configured in accordance with the invention;

FIG. 5 comprises a depiction of overlapping depth of fields in an embodiment configured in accordance with the invention;

FIG. 6 comprises a depiction of non-overlapping depth of fields in an embodiment configured in accordance with the invention;

FIG. 7 comprises a side elevational view of another embodiment configured in accordance with the invention;

FIG. 8 comprises a top plan view of a composite virtual microscope slide;

FIG. 9 comprises a perspective view of a symbolic model of a virtual microscope slide as configured in accordance with the invention;

FIG. 10 comprises a flow diagram configured in accordance with an embodiment of the invention; and FIG. 11 comprises a flow diagram detail as configured in accordance with another embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Some features may also be depicted in limited numbers and common elements may be omitted for purposes of brevity and clarity.

DETAILED DESCRIPTION OF THE PREFERRED EMBODIMENTS

FIG. 3 is a block diagram of a system according to the invention for acquiring a virtual microscope slide, that includes a Z-axis image dimension across the entire virtual slide. The system includes a microscope subsystem 15 with a digitally controlled stage platform 28 for supporting the glass microscope slide 21. The digital stage platform 28 can operate over a large number of increments to position the stage in the horizontal x and y plane with high precision. A glass microscope slide or other substrate 21 is placed on the stage 28. The system also includes a controlling computer system 32 with a keyboard 37, a mouse 38 with a mouse wheel control 39, and a display monitor 40. The controlling computer system keyboard and mouse are used via the automatic focus step size setup window 12 to input the automatic focus step size parameters and the Z Stack step size setup window 13 is used to input the Z Stack step size parameters.

FIG. 3A shows the focus setup step size 55 input control. Also in FIG. 3A are shown the associated setup controls for the frequency of focus 56, a threshold for controlling whether automatic focus should be performed on a specific field of view, and a control 58 to manually increment the Z-axis dimension to move the microscope stage 28 up or down vertically in incremental units. As may be appreciated by the foregoing description, and the following descriptions, and as is well known in the art, the control of focus at high magnification and small depth of field is complicated and involves many variables. It is also time consuming if performed on every specimen image field of view in constructing or capturing a virtual microscope slide image data set. Therefore, in the preferred embodiment and in the subsequently described alternative embodiments there are additional control and setup parameters to overcome major variables and to enable a faster overall virtual slide scan capture time. Some of these are seen in FIG. 3A. For example, the frequency of focus 56 parameter allows automatic focus to occur on every adjacent field of view if it is set to 1, or on every other field if it is set to 2, etc. In the following detailed description the assumption is that the frequency of focus is set to 1. However, if it is set to a higher number the reference tiles of field of views not focused take the default focus contrast value of the last previous focused image tile. In the alternate embodiments of the invention, the reference tile position is sometimes obtained in a different fashion as described for those embodiments. There is a significant speed of scan advantage related to not focusing on every field of view. However, on many specimens the disadvantage is that the resulting scan may not have an optimum depth of field position for the reference image. It may also be appreciated that one of the Z Stack images may then offer a more optimum image for the final remote viewer of the images. Also, often there is not enough image structure in a field of view to obtain an automatic focus, for example in the case of a substantially blank or empty field of view. In that case the control 57 allows for a focus contrast threshold value input parameter that can be checked to allow skipping such fields. Also, in that instance the default reference Z-axis position for the next image requiring focus is the last previous focused image tile.

FIG. 3B shows the Z Stack step size 60 input control. It may be appreciated that there are a multitude of factors that would require this parameter to be changed for a specific specimen. However, the most important of these is usually the magnification of the specific microscope objective lens being used, since each lens has a different depth of field specification, in combination with the type of specimen and estimated thickness of the specimen preparation. Also, shown in FIG. 3B is a checkbox control 59 to either enable or disable the Z Stack image save for a specific virtual microscope data capture scan.

According to the teachings of the aforesaid patent the computer controlled microscope is moved to start a scan of the entire specimen object 31 using the stage controller 14 to move the precision stage 28 to a new objective lens 10 field of view to acquire an initial image at that position and compute a focus contrast parameter on that image. According to the present invention the relative Z-axis reference position for the first new field of view image tile is obtained by an iterative automatic focus procedure. The controlling computer system 32 sends the microscope subsystem 15 Z-axis control signals to change the Z-axis position control to move the stage incrementally to go up 4 times in the automatic focus step size and then to go down 4 times in automatic focus step size. At each incremental change in the Z-axis position the image acquisition electronics 17 are controlled to acquire an image. A focus contrast parameter is computed on each image. The automatic focus Z-axis position is then determined by choosing the Z-axis position associated with the largest value of the focus parameter from the initial reference image and the set of 8 images. If the largest value is at one end of the sequence, i.e. the 4.sup.th image down or the 4t image up from the reference image, that image becomes the reference image, and the procedure is recursively repeated until the largest focus contrast value is found in the middle range of the sequence of images, i.e. not at either end image. This becomes the relative Z-axis reference position for the new field of view image. As explained more fully in the following, the image tile associated with this relative Z-axis position is then stored in the virtual slide data structure.

In the preferred embodiment of the invention the controlling computer system is operated under a Windows Operating System (Microsoft Corporation, Redmond, Wash., USA). Referring to FIG. 3A, the virtual microscope slide data structure is stored as a Windows Operating System file folder where each tiled image is a .jpg image file with an incremental image name automatically assigned by the controlling computer systems software program. The .jpg image names are numbered so that the first acquired image is called DA0.jpg, the second DA1.jpg, the third DA3, etc. In FIG. 3C there is depicted a virtual slide data folder 42 with portions of the data structure 43, 44, 45, 46, and 47 also depicted. The set of 9 image tiles 43, 45 and 46 named DA98 are associated with a specific X, Y specimen image plane position, and an adjoining set 44 and 48, named DA99 are associated with another abutted specific X, Y specimen image plane position. The two reference tiles are depicted as 43 and 44 for the data structure at the two X, Y locations. These tiles are in the automatic focus determined Z-axis position, and the recorded .jpg image contains the depth of field image structure associated with that Z-axis position and the field of view at the respective X, Y location.

During the system program operation to produce a virtual microscope slide, the controlling computer system also creates an additional text information file of the Windows Operating System format .ini. As depicted in FIG. 3C, this file 47 is named FinalScan.ini. Among other things this file contains a list of names corresponding to each reference tile in the virtual microscope data structure. For each reference tile in the list, that tiles X, Y, and Z digital location is tabulated. As taught in the aforementioned patent this information is then used by the virtual Internet server and virtual microscope visual display programs to abut and reconstruct the various tiled images to allow a remote viewer to view contiguous regions of virtual slide images. It may be appreciated that the components of the data structure shown by example in FIG. 3C may be stored in a database or any other form allowing rapid sequential access to the reference image and the full Z Stack components. A novel aspect of this data structure is the close association of these image components. This greatly facilitates client server interactions in remote Internet viewing. Since the this subsequent viewing is through the limited X, Y planar view of an image display device, only a few reference tiles (and in certain limited situations only one reference tile) may be in the available user view for a focus request to the server. As will be appreciated in the following description, this type of data structure facilitates rapid transmission of Z-axis image content to the client computer. Some Internet server computers facilitate serving very large images requiring zooming, by using a pyramid data structure where different levels of image zoom are pre-constructed from the original image and kept in memory or virtual memory at one time. This requires a very large amount of memory when considering the requirement of keeping multiple planes of such image structures, such as shown conceptually in FIG. 9. The data structure of this invention is much more efficient when used specifically for virtual microscope slides with special viewing programs, since it in essence is pre-constructed to serve reference and z Stack images rapidly from memory or digital disk storage in these small reference and Z Stack image units.

After capturing a relative tile for the Z-axis position at a given X, Y specimen plane position the system of the invention proceeds to use the Z-axis step size and execute the Z Stack save procedure. To accomplish this, the controlling computer system 32 is directed to control the Z-axis positioning control 16 of the microscope subsystem 15 first to move down the Z-axis in incremental Z-axis step sizes, and at each step to acquire an image tile. These image tiles 45 are stored in the data structure depicted in FIG. 3 by example for the data-structure set DA98. Secondly, the controlling computer system 32 is directed to control the Z-axis positioning control 16 of the microscope subsystem 15 to move up the Z-axis in incremental Z-axis step sizes from the reference Z-axis position, and at each step to acquire an image tile. These image tiles 46 are stored in the data structure depicted in FIG. 3 by example for the data structure set Da98.

The same series of events described above for the data structure capture of the tile set Da98 is repeated for all field of views associated with the capture of the virtual microscope slide. For example, in FIG. 3 as the data structure set Da99, and so forth.

The result of the above described preferred embodiment of the system of the invention is in effect to first factor out, or neutralize, the Z-axis irregularities in optimum focus position over the X, Y surface of the slide for the initial relative captured image tile, and then, secondly to create a set of cohesive Z-axis dimensioned captured image planes, where each plane relates to a different, real, physical depth of field position in the specimen. The first relative Z-axis positioning has brought into parallel positioning capture, the optimum depth of field portions of each specimen, and the Z Stack capture has resulted in image planes above and below that. This image sequence sampling can be reconstructed from the data structure storage elements 43, 44, 45, 46, and 48 when used with the X, Y location information stored in data structure element 47. This reconstruction is depicted in an idealized fashion as shown in FIG. 4 in cross section and in FIG. 9 in perspective schematic, as an aid in visualizing the resulting complete virtual microscope slide data structure. As described below, in fact only a small portion of this is seen by the remote viewer at one time, because of the limitations of the image display of commonly used computer screens. However, it is all available for viewing by scrolling and requesting additional image tiles from a virtual microscope slide server.

It will be appreciated by those familiar with the art that the above preferred description of the embodiment of the invention may be modified in other ways to enable the creation of a virtual microscope slide with Z-axis image dimension information. In this regard, an alternative method of practicing the invention is described. This method is more applicable for specimen objects that don't cover a large area, or in those instances where the stage platform 28 and microscope slide 21 are positioned to present the specimen 31 in a reasonably flat plane, or where a lower power objective is used that has a larger depth of field. For a given level of magnification (such as 10× for example) the microscope objective 10 with associated video camera is adjusted up or down, or as in the preferred embodiment, the stage is adjusted up or down, either adjustment to bring into view an initial reference image into the focal plane depth of field of the microscope objective 10 and used to create magnified images of the specimen 31 for a given X, Y position in the specimen plane. A first series of planar abutted image tiles are obtained as described in the preferred embodiment as the reference tile set, and stored in the data structure previously described, and as shown by example in FIG. 3C, wherein the example reference tiles 43 and 44 are depicted. The reference tiles Z-axis position in this embodiment are computed using the results of a prior setup procedure where the Z-axis positions at three separate places on a specimen are determined and a mathematical Z-axis plane is determined across the X, Y plane of the specimen by computations involving fitting a plane in the Z-axis by using three X, Y points with known Z-axis values. In this case during the scanning process this computed position is used instead of the iterative, recursive, automated focus procedure described in the first preferred method. This results in a faster scan and image capture process.

By way of illustration the capture of the complete set of tiles in this plane may be visualized in cross section as the depth of field 41 in FIG. 4. This scan captures the upper surface of much of the specimen 31. Then, in accordance with this embodiment, the stage Z-axis position is changed according to one Z Stack increment and another series of images are captured and stored in the data structure shown in FIG. 3. For example, if the first series of images used the focal distance corresponding depth of field represented by reference numeral 43, then by decreasing the stage Z-axis position relative to the microscope objective, the next series of images would be represented by reference numeral 46a. Conversely, by increasing the stage Z-axis position relative to the microscope objective the next series of images would be represented by reference numeral 45a. Subsequent series of images can likewise be captured by positioning different Z-axis planes in the depth of field region of the objective. In the embodiment depicted in FIG. 4, in addition to the original image series captured 43, two other series represented by reference numerals 46a and 46b and two additional series represented by reference numerals 45a and 45b are also captured. By capturing and storing these additional images from different regions of the specimen, a virtual focusing capability can be realized as described below in more detail. It may also be realized that this method of scanning may be more suited to a type of triple pixel line sensor described above as a 3 by 2098 sensor. Sometimes this is referred to as a single line sensor. In this case since small discrete individual tiles are not available, the prediction of a reference plane by computation, or simple assumption of a completely flat and parallel X, Y-plane may be preferred. This type of scan results in saving images of longer strip tiles, with a width of 2098 pixels inside the field of view of the microscope objective 10 in one direction, but the saved images extending beyond the field of view by continuous scanning and storing in the other direction. The abutted 2098 pixel wide strip tiles taken together side by side form a virtual microscope slide.

Also as illustrated in FIG. 4, there are two focal depth of fields above and two focal depth of fields below, both provided with respect to the initial reference setting. In a given application, it may be appropriate to provide only a single additional set of images using only one slightly different focal depth of field (or focal plane) above and below. For most purposes, however, images captured at a plurality of differing focal planes are appropriate. In the preferred embodiment, four focal planes above and four focal planes below are used in addition to the original reference focal plane to provide a total of nine sets of focal plane images. Wherein each set of focal plane images corresponds to a given focal distance from the reference setting and all of the sets share the same level of magnification. By providing this many sets both above and below the reference focal plane, relatively smooth and detailed virtual focusing can be realized that well mimics the look and feel of focusing with an actual microscope within a useful range of focusing.

As described in the above, the various depths of field substantially abut one another. In an alternative embodiment, and as illustrated in FIG. 5, a given depth of field 51 for a given series of images can partially overlap with another depth of field 52 for a different series of images. Or, if desired and as illustrated in FIG. 6, different depths of field 61 and 62 as corresponding to different image series can neither overlap nor abut one another. Instead, a small gap can exist between the two fields. In general, adjusting the focal distances such that the fields are substantially adjacent one another with little or no overlap probably represents an optimum configuration, but the other alternatives may be useful for some purposes depending upon user requirements.

With reference to FIG. 7, an initial focal plane 71 (as initially determined manually or predetermined manually or automatically) having a corresponding depth of field 41A may be appropriately used when imaging a particular section of a specimen (not shown) that is within the field of view when the microscope is located in a first position 10A. That is, when the microscope is so positioned, this initial focal distance 71 represents an optimum focus by whatever standard the user applies. In accordance with the various embodiments above, one or more additional images are also taken of this same field of view with slightly different focal distances. At another portion of the slide, however, when the microscope is positioned at a second position 10B, it may be that a different initial focal plane 72 will yield an optimum focus when using the same standard as was applied earlier. This different initial focal distance 72 will have a corresponding depth of field 41B that is substantially identical in size to the depth of field 41A for the first position's initial focal distance 71 but that is positioned a different distance from the slide 21. This is often the case when imaging tissue microarray (TMA) cores as described in U.S. Pat. No. 6,466,690 B2 (entitled Method and Apparatus for Processing an Image of a Tissue Sample Microarray). There the image capture is from a great many different objects, TMA cores, arranged over essentially the entire surface of the glass microscope slide. Therefore, while the resulting images still comprise a abutted composite representations of the object, they refer to different reference image focal planes. And, according to this embodiment, regardless of differences as may exist between the initial focal reference focal plane from object to object, each resulting image will nevertheless have an identical number of Z Stack focal planes available for fine focusing by a user.

As discussed above, virtual microscope slides, whether created from many small tiles as in the preferred embodiment, or whether created in strips of line segments, and whether they are stored in a tiled data structure or whether they are stored as one large reconstructed image in memory, such as one focal plane from the set of 5 focal planes 91 in FIG. 9, cannot usually be viewed in their entirety at the original captured resolution because of the finite size and pixel dimensions of a remote viewers computer display screen. As depicted in FIG. 8, one prior art approach that is useful in this regard utilizes a plurality of individual images 83, referred to as tiles, to form a larger composite image of the slide 81 and the specimen 82. U.S. Pat. No. 6,396,941 B1 (entitled Method and Apparatus for Internet, Intranet and Local Viewing of Virtual Microscope Slides), the contents of which are incorporated herein by this reference, teaches the Internet or intranet display of virtual microscope slides. As taught therein, a virtual microscope slide typically comprises a digitized magnified view of part or all of a microscope slide and an object (such as a biological specimen) disposed thereon. The aforementioned patent also teaches various Internet server and thin client, and other Java Applet and ActiveX viewer methods enabling the reconstruction of the virtual microscope image content for a remote viewer. It will be appreciated that the viewing of a single focal plane depth of view is accomplished whether the image is stored as a tiled database structure or as a complete single image plane in computer core memory. In the preferred embodiment of this invention however, when the remote viewer sends a request to the server for a reference image tile focus for a defined region of interest, the server also sends the associated Z Stack images all in sequence for that region of interest. The associated Z Stack images are cached by the local computer so that a smooth and rapid local viewing can simulate the analog optical focusing operation of a real microscope.

Referring now to FIG. 10, in one embodiment, a user can employ a standard computing platform to interface to the virtual slide server and data storage facility that retains the virtual microscope slide information as described above for a given specimen. A standard client/server model works well to facilitate such a relationship, but other data transfer mechanisms can be used as well as appropriate to a given application. The relevant process begins with a user platform retrieving 101 a desired image at a particular magnification × (such as, for example, 40×). As described in the aforementioned patent, all images for the object need not be immediately retrieved and made available locally. To minimize network transactions, in fact, only the data required to display a single field of view need to be immediately retrieved and displayed. In the system and method of the current invention and the various embodiments above, each field of view has a corresponding plurality of images with each image representing a different focal plane. Therefore, when retrieving and displaying the first image, one of these images must be selected first. In the preferred embodiment the selection is the reference image set corresponding to those tiles that will fill the view window of the remote viewers image display screen. Also, the associated Z Stack images for each reference tile are transmitted and cached in the local computer. In one embodiment, where the initial automatically determined optimum focal plane image is flanked on each side by four different focal plane images, the initial image itself can be automatically selected for initial retrieval 101 and display 102. The process then monitors 103 for instructions from the user to modify the focus. When no such instruction appears, the process continues 104 in accordance with whatever other functions are supported (for example, input from the user indicating a desire to scroll the image in a particular direction can be received and used to cause retrieval and display of corresponding images). When a focus modification instruction is received, however, the process retrieves 105 the image from the local memory cache for that field of view that corresponds to the instruction and displays 106 it. Pursuant to one embodiment, the user can be limited to moving the focus in a step by step process with a mouse wheel 93 or keyboard 37 up or down arrow keys, such that each increment causes retrieval and display of the next adjacent image in the Z-axis dimension. In the preferred embodiment the user, or remote viewer, can move about and focus on the virtual microscope slide with a wheeled mouse control, essentially as one moves about and focuses with a physical microscope and slide. With this capability, a wide variety of specimens can be readily viewed with good results. Not only can the resultant virtual microscope slides be used for educational and training purposes, but also for both qualitative and quantitative analysis purposes in support of various diagnostic processes. With reference to FIG. 11, pursuant to one optional embodiment, when a user seeks to modify 103 the focus as described, the process can determine 111 whether a focusing limit has been reached. For example, if the user platform has already retrieved and displayed the image that was captured using the focal plane at the furthest Z-axis dimension from the reference tile and the user is now instructing the platform to focus on an even further distance, the present display can be maintained 112. Optionally, a text message or other indicator can be provided 113 to the user to alert the user that the focus limit has been reached. In another embodiment, a visual indicator can be provided to the user to indicate a present focusing position within a range of focusing possibilities, such that the user can ascertain for themselves such a condition.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. It is intended in the appended claims to cover all those changes and modifications which fall within the true spirit and scope of the present invention.

What is claimed is:

1. An apparatus for viewing a virtual microscope slide data structure containing images of a specimen, the apparatus comprising:

a control system configured to retrieve images from the virtual microscope slide data structure and construct a composite image of a portion of the specimen based on at least a portion of the first or second set of images, the data structure comprising a first and second set of contiguous non-overlapping images of the specimen, and coordinating information that relates positions of the first and second set of images, wherein a plurality of images in the first set of images are associated with a first focal plane and a plurality of images in the second set of images are associated with a second focal plane, wherein the second focal plane is displaced relative to the first focal plane.

2. The apparatus of claim 1 wherein the control system is configured to retrieve the first and second plurality of images over an Internet or intranet transmission channel.

3. The apparatus of claim 1 wherein the control system is configured to construct a composite image at the first focal plane based on the first plurality of images and the coordinating information.

4. The apparatus of claim 1 wherein the control system is configured to construct a composite image at the second focal plane based on the second plurality of images and the coordinating information.

5. The apparatus of claim 1 wherein control system is configured to receive a focus input and select at least a portion of the first or second set for construction of the composite image.

6. The apparatus of claim 1 further comprising an Internet browser configured to manipulate the first and second set of images.

7. The apparatus of claim 6 further comprising an applet configured to manipulate the first and second set of images.

8. The apparatus of claim 1 wherein control system is configured generate a first composite image based on the first set of images and a second composite image based on the second set of images, the control system being configured to switch between the first and second composite images to simulate focusing up or down.

9. The apparatus of claim 1 wherein each image in the first set of images is associated with a unique x, y planar position of the specimen.

10. The apparatus of claim 1 wherein the first focal plane and the second focal plane have depths of field that are at least partially overlapping.

11. The apparatus of claim 1 wherein the first focal plane and the second focal plane have depths of field that are at least partially abutting.

12. The apparatus of claim 1 wherein the first focal plane and the second focal plane have depths of field that are non-overlapping.

13. An method of viewing a virtual microscope slide data structure containing images of a specimen, the method comprising:

retrieving images from the virtual microscope slide data structure, and constructing a composite image of a portion of the specimen based on at least a portion of the first or second set of images, the data structure comprising a first and second set of contiguous non-overlapping images of the specimen, and coordinating information that relates positions of the first and second set of images, wherein a plurality of images in the first set of images are associated with a first focal plane and a plurality of images in the second set of images are associated with a second focal plane, wherein the second focal plane is displaced relative to the first focal plane.

14. The method of claim 13 further comprising retrieving the first and second plurality of images over an Internet or intranet transmission channel.

15. The method of claim 13 further comprising constructing a composite image at the first focal plane based on the first plurality of images and the coordinating information.

16. The method of claim 13 further comprising constructing a composite image at the second focal plane based on the second plurality of images and the coordinating information.

17. The method of claim 13 further comprising receiving a focus input and selecting at least a portion of the first or second set for construction of the composite image.

18. The method of claim 13 further comprising:
generating a first composite image based on the first set of images and a second composite image based on the second set of images; and
switching between the first and second composite images to simulate focusing up or down.

19. The method of claim 13 wherein each image in the first set of images is associated with a unique x, y planar position of the specimen.

20. The method of claim 13 wherein the first focal plane and the second focal plane have depths of field that are at least partially overlapping.

21. The method of claim 13 wherein the first focal plane and the second focal plane have depths of field that are at least partially abutting.

22. The method of claim 13 wherein the first focal plane and the second focal plane have depths of field that are non-overlapping.

* * * * *